(12) United States Patent
Stergiades et al.

(10) Patent No.: US 7,557,247 B2
(45) Date of Patent: Jul. 7, 2009

(54) CRYSTALLINE FORM OF $\beta_2$ ADRENERGIC RECEPTOR AGONIST

(75) Inventors: Ioanna Stergiades, San Francisco, CA (US); Edward Yost, Santa Clara, CA (US)

(73) Assignee: Theravance, Inc., South San Francisco, CA (US)

( * ) Notice: Subject to any disclaimer, the term of this patent is extended or adjusted under 35 U.S.C. 154(b) by 0 days.

(21) Appl. No.: 10/854,405

(22) Filed: May 26, 2004

(65) Prior Publication Data

US 2004/0248985 A1  Dec. 9, 2004

Related U.S. Application Data

(60) Provisional application No. 60/473,423, filed on May 27, 2003.

(51) Int. Cl.
*C07C 233/03* (2006.01)
*A61K 31/16* (2006.01)

(52) U.S. Cl. .................. 564/223; 514/461; 514/625; 514/629; 549/483; 549/484

(58) Field of Classification Search .............. 514/461, 514/625, 629; 564/223; 549/483, 484
See application file for complete search history.

(56) References Cited

U.S. PATENT DOCUMENTS

| 4,151,354 | A * | 4/1979 | Krapcho | 544/159 |
| 6,537,983 | B1 * | 3/2003 | Biggadike et al. | 514/172 |
| 6,541,669 | B1 | 4/2003 | Moran et al. | |
| 6,576,793 | B1 * | 6/2003 | Moran et al. | 564/223 |
| 6,670,376 | B1 | 12/2003 | Moran et al. | |
| 6,683,115 | B2 | 1/2004 | Moran et al. | |
| 6,759,398 | B2 | 7/2004 | Biggadike | |
| 2002/0019378 | A1 | 2/2002 | Angell et al. | |
| 2005/0075271 | A1 * | 4/2005 | Linsell et al. | 514/1 |

FOREIGN PATENT DOCUMENTS

| WO | WO 01/42193 A1 | 6/2001 |
| WO | WO 02/066422 A1 | 8/2002 |
| WO | WO 02/070490 A1 | 9/2002 |
| WO | WO 02/076933 A1 | 10/2002 |
| WO | WO 03/024439 A1 | 3/2003 |
| WO | WO 03/042164 A1 | 5/2003 |
| WO | WO 03/072539 A1 | 9/2003 |
| WO | WO 03/091204 A1 | 11/2003 |
| WO | WO 2004/011416 A1 | 2/2004 |

OTHER PUBLICATIONS

Gould, "Salt selection for basic drugs", International Journal of Pharmaceutics, vol. 33, No. 1/3, pp. 201-217 (1986).
U.S. Appl. No. 11/654,117, Sterglades et al.
Berge et al., "Pharmaceutical Salts", Journal of Pharmaceutical Sciences, vol. 66, No. 1, pp. 1-19 (1977).
Li et al., "Relationship Between Physical Properties and Crystal Structures of Chiral Drugs", Journal of Pharmaceutical Sciences, vol. 86, No. 10, pp. 1073-1078 (1997).

* cited by examiner

*Primary Examiner*—Shailendra Kumar
(74) *Attorney, Agent, or Firm*—Jeffrey A. Hagenah; Roberta P. Saxon

(57) ABSTRACT

The invention provides a novel $\beta_2$ adrenergic receptor agonist in crystalline salt form. The invention also provides pharmaceutical compositions comprising the novel $\beta_2$ adrenergic receptor agonist in crystalline salt form, formulations containing the pharmaceutical compositions, methods of using the crystalline salt to treat diseases associated with $\beta_2$ adrenergic receptor activity, and processes useful for preparing such crystalline compounds.

16 Claims, 2 Drawing Sheets

CRYSTALLINE FORM OF β₂ ADRENERGIC RECEPTOR AGONIST

CROSS-REFERENCE TO RELATED APPLICATIONS

This application claims the benefit of U.S. Provisional Application No. 60/473,423, filed on May 27, 2003, the disclosure of which is incorporated herein by reference in its entirety.

FIELD OF THE INVENTION

The invention is directed to a β₂ adrenergic receptor agonist in crystalline salt form. The invention is also directed to pharmaceutical compositions comprising the crystalline agent, formulations containing the pharmaceutical compositions, methods of using the crystalline agent to treat diseases associated with β₂ adrenergic receptor activity, and processes useful for preparing such a crystalline compound.

BACKGROUND OF THE INVENTION

β₂ Adrenergic receptor agonists are recognized as effective drugs for the treatment of pulmonary diseases such as asthma and chronic obstructive pulmonary disease (including chronic bronchitis and emphysema). β₂ Adrenergic receptor agonists are also useful for treating pre-term labor, and are potentially useful for treating neurological disorders and cardiac disorders. Commonly assigned U.S. Pat. No. 6,576,793 B1 discloses the novel compound N-{2-[4-((R)-2-hydroxy-2-phenylethylamino)phenyl]ethyl}-(R)-2-hydroxy-2-(3-formamido-4-hydroxyphenyl)ethylamine,

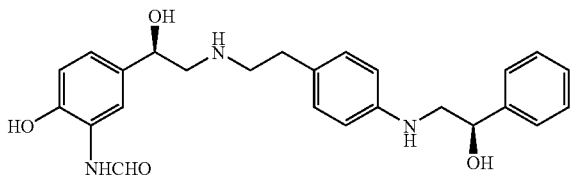

1 as a potent β₂ adrenergic receptor agonist. Compound 1 is alternatively referenced by the chemical names N-[3-[(1R)-1-hydroxy-2-[[2-[4-[((2R)-2-hydroxy-2-phenylethyl)amino]phenyl]ethyl]amino]ethyl-6-hydroxyphenyl]-formamide, (α-R)-3-formamido-4-hydroxy-α-[[[p-(N-((2R)-hydroxy-phenethyl))-amino-phenethyl]amino]methyl benzyl alcohol, and N-[2-hydroxy-5-[(1R)-1-hydroxy-2-[[2-[4-[[(2R)-2-hydroxy-2-phenylethyl]amino]phenyl]ethyl]amino]ethyl]phenyl]-formamide.

Active agents for the treatment of pulmonary diseases are advantageously administered by inhalation. Preparation of formulations for administration by inhalation typically relies on the existence of a crystalline form of the active agent, or of a crystalline form of a pharmaceutically acceptable salt of the active agent, having suitable physical and chemical properties. For example, crystalline salts used in formulations administered by inhalation typically must be non-hygroscopic and thermally stable. Thus it would be desirable to provide a crystalline form of compound 1 or of a salt thereof that is stable upon storage even under conditions of elevated temperature and relative humidity.

SUMMARY OF THE INVENTION

The present invention provides crystalline N-{2-[4-((R)-2-hydroxy-2-phenylethylamino)phenyl]ethyl}-(R)-2-hydroxy-2-(3-formamido-4-hydroxyphenyl)ethylamine monohydrochloride. A crystalline monohydrochloride salt of compound 1 has been characterized by x-ray powder diffraction (XRPD), differential scanning calorimetry (DSC), infrared spectroscopy (IR), nuclear magnetic resonance spectroscopy (NMR), and by elemental analysis.

The monohydrochloride salt of compound 1 has been found to be neither hygroscopic nor deliquescent, even when exposed to the atmosphere for prolonged periods at high relative humidity; and to be thermally stable at elevated temperatures.

The invention also provides pharmaceutical compositions comprising the monohydrochloride salt of compound 1 and a pharmaceutically acceptable carrier. The pharmaceutical compositions include formulations that are specifically prepared for administration by inhalation. Further, the invention provides combinations comprising the monohydrochloride salt of compound 1 and one or more other therapeutic agents and pharmaceutical compositions comprising such combinations.

In another aspect, the invention provides a method of treating a disease or condition associated with β₂ adrenergic receptor activity (e.g. a pulmonary disease, such as asthma or chronic obstructive pulmonary disease, pre-term labor, a neurological disorder, a cardiac disorder, or inflammation) in a mammal, the method comprising administering to the mammal, a therapeutically effective amount of the monohydrochloride salt of compound 1. The invention also provides a method of treatment comprising administering a combination of a therapeutically effective amount of the monohydrochloride salt of compound 1 together with one or more other therapeutic agents.

The invention further provides the monohydrochloride salt of compound 1 for use in medical therapy, as well as the use of the monohydrochloride salt of compound 1 or of a pharmaceutical composition comprising the monohydrochloride salt of compound 1 in the manufacture of a medicament for treating a disease or condition associated with β₂ adrenergic receptor activity in a mammal.

In yet another aspect, the invention provides a process for preparing the crystalline monohydrochloride salt of compound 1, comprising the steps of dissolving N-{2-[4-((R)-2-hydroxy-2-phenylethylamino)phenyl]ethyl}-(R)-2-hydroxy-2-(3-formamido-4-hydroxyphenyl)ethylamine in a polar solvent to form a first solution; and adding aqueous hydrochloric acid containing between about 0.9 and about 1 mole of chloride ions per mole of compound 1 to form a second solution, from which the monoHCl salt is formed by crystallization. Alternative methods of forming the present monoHCl salt are also provided as additional aspects of the invention.

BRIEF DESCRIPTION OF THE DRAWINGS

The invention is illustrated by reference to the accompanying drawings.

DETAILED DESCRIPTION OF THE INVENTION

Figure 1:
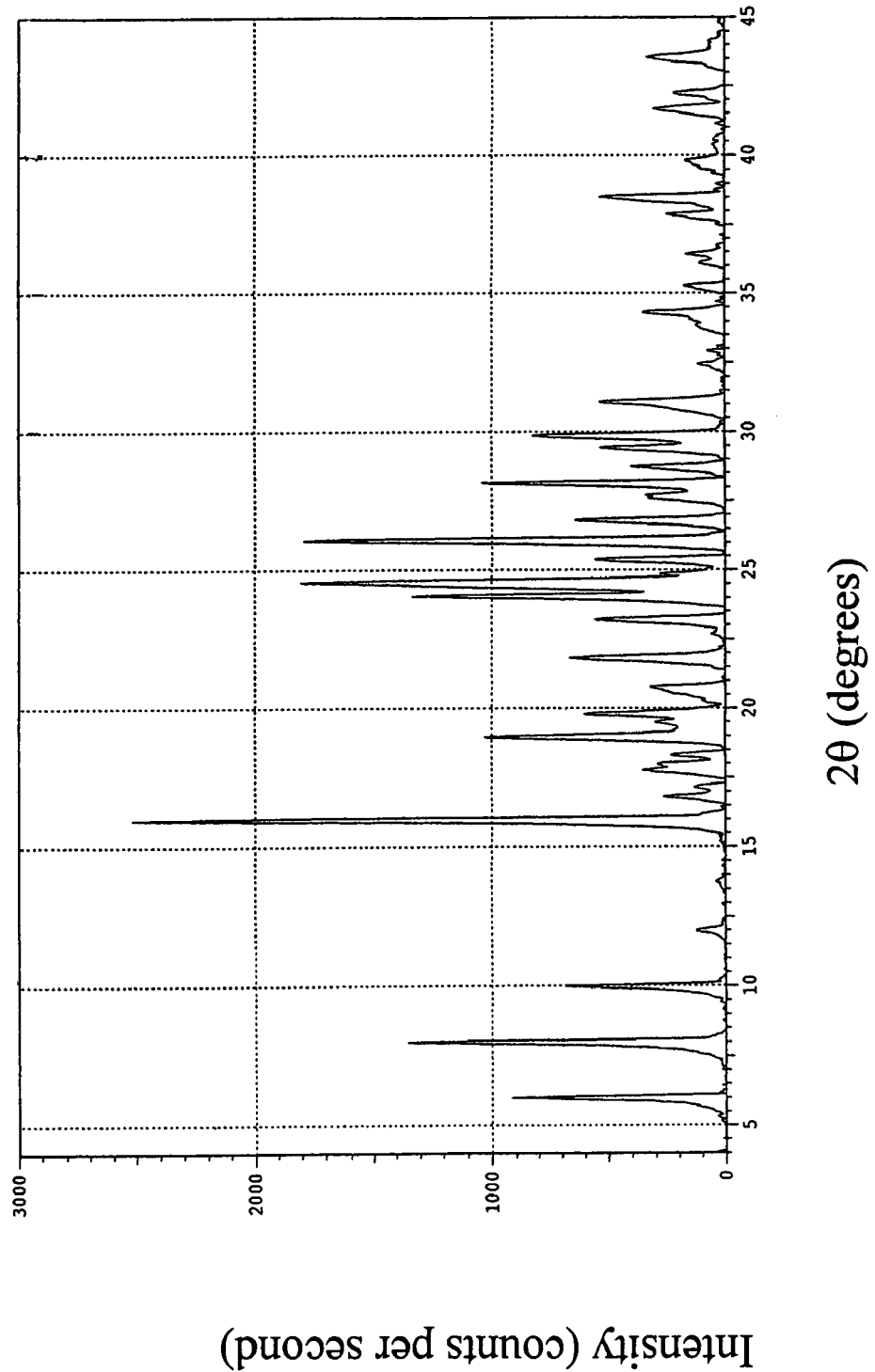
FIG. 1 shows an x-ray powder diffraction pattern of N-{2-[4-((R)-2-hydroxy-2-phenylethylamino)phenyl]ethyl}-(R)-2-hydroxy-2-(3-formamido-4-hydroxyphenyl)ethylamine monohydrochloride.

When describing the compounds, compositions and methods of the invention, the following terms have the following meanings, unless otherwise indicated.

The term "therapeutically effective amount" refers to an amount sufficient to effect treatment when administered to a patient in need of treatment.

The term "treatment" as used herein refers to the treatment of a disease or medical condition in a patient, such as a mammal (particularly a human) which includes:

(a) preventing the disease or medical condition from occurring, i.e., prophylactic treatment of a patient;
(b) ameliorating the disease or medical condition, i.e., eliminating or causing regression of the disease or medical condition in a patient;
(c) suppressing the disease or medical condition, i.e., slowing or arresting the development of the disease or medical condition in a patient; or
(d) alleviating the symptoms of the disease or medical condition in a patient.

The phrase "disease or condition associated with $\beta_2$ adrenergic receptor activity" includes all disease states and/or conditions that are acknowledged now, or that are found in the future, to be associated with $\beta_2$ adrenergic receptor activity. Such disease states include, but are not limited to, bronchoconstrictive or pulmonary diseases, such as asthma and chronic obstructive pulmonary disease (including chronic bronchitis and emphysema), as well as neurological disorders and cardiac disorders. $\beta_2$ Adrenergic receptor activity is also known to be associated with pre-term labor (see U.S. Pat. No. 5,872,126) and some types of inflammation (see WO 99/30703 and U.S. Pat. No. 5,290,815).

It must be noted that, as used in the specification and appended claims, the singular forms "a", "an", "one", and "the" may include plural references, unless the content clearly dictates otherwise.

The present invention provides crystalline N-{2-[4-((R)-2-hydroxy-2-phenylethylamino)phenyl]ethyl}-(R)-2-hydroxy-2-(3-formamido-4-hydroxyphenyl)ethylamine monohydrochloride. In one embodiment, a crystalline form of the present invention is characterized by an x-ray powder diffraction (XRPD) pattern having two or more diffraction peaks at 2θ values selected from the group consisting of 6.00±0.2, 7.99±0.2, 9.98±0.2, 15.98±0.2, 24.05±0.2, 24.53±0.2, 25.35±0.2, 26.08±0.2, 26.77±0.2, 28.13±0.2, 34.31±0.2, and 38.49±0.2. In particular, in this embodiment, the crystalline form is characterized by an x-ray powder diffraction pattern having two or more diffraction peaks at 2θ values selected from the group consisting of 15.98±0.2, 24.05±0.2, 26.08±0.2, and 28.13±0.2.

As is well known in the field of x-ray powder diffraction, relative peak heights of XRPD spectra are dependent on a number of factors having to do with sample preparation and instrument geometry, while peak positions are relatively insensitive to experimental details. Thus, in one embodiment, a crystalline monoHCl salt of compound 1 is characterized by an x-ray powder diffraction pattern in which the peak positions are substantially in accordance with those shown in FIG. 1.

In another embodiment, a crystalline form of the active salt is characterized by its infrared absorption spectrum which shows significant absorption bands at about 699, 788, 810, 827, 875, 970, 1026, 1056, 1080, 1101, 1213, 1296, 1374, 1441, 1546, 1596, 1660, 3371, and 3553 cm$^{-1}$. Variability in infrared absorption peak positions is typically within an uncertainty of ±2 cm$^{-1}$, preferably within an uncertainty of +1 cm$^1$.

Figure 2:
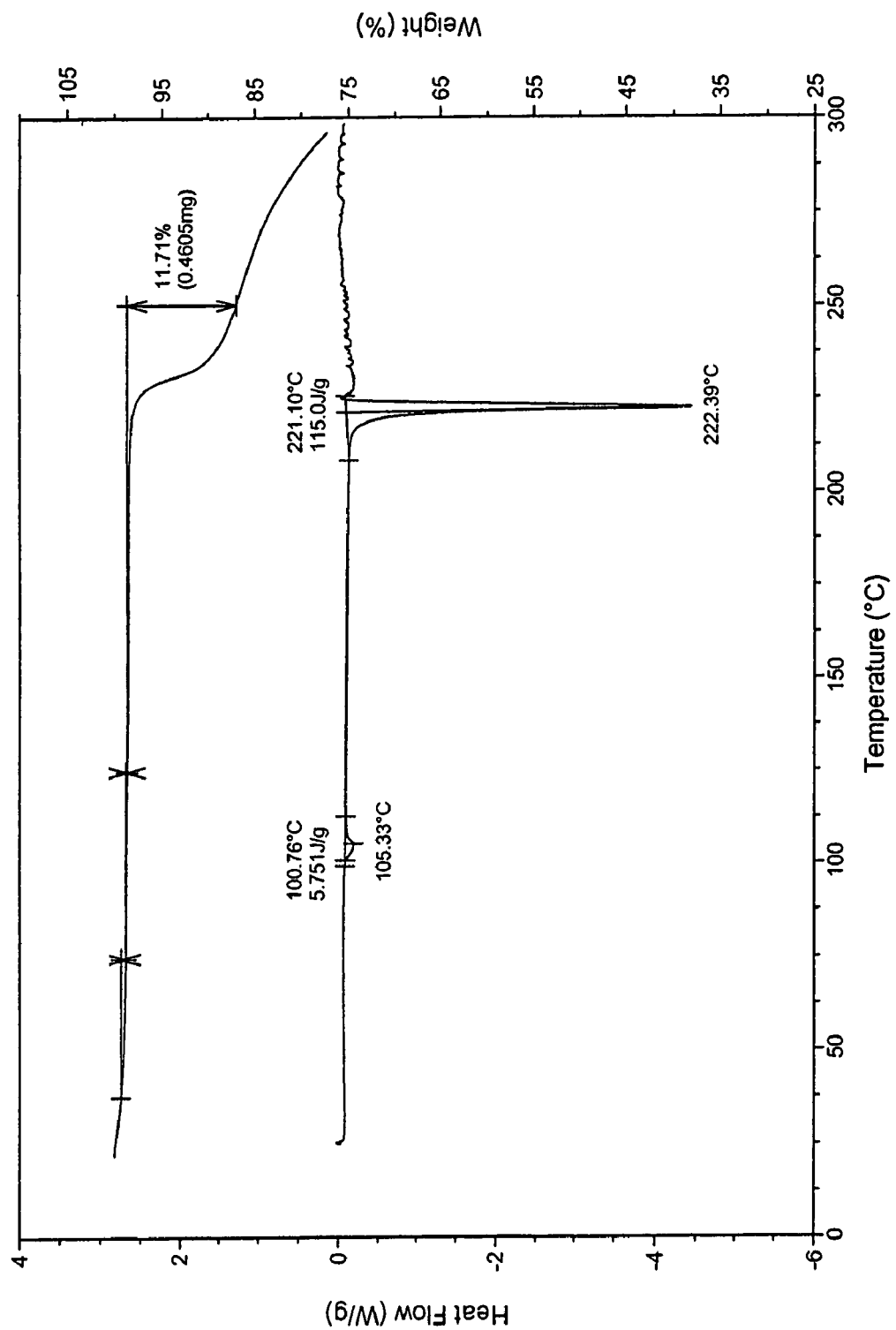
FIG. 2 shows a differential scanning calorimetry trace in which the positive scale represents exothermic heat flow (bottom trace, left side scale) and thermogravimetric trace (top trace, right side scale) of N-{2-[4-((R)-2-hydroxy-2-phenylethylamino)phenyl]ethyl}-(R)-2-hydroxy-2-(3-formamido-4-hydroxyphenyl)ethylamine monohydrochloride.

In yet another embodiment, a crystalline monoHCl salt of the present invention is characterized by its differential scanning calorimetry trace which shows a minor endothermic feature between about 95 and 115° C. and an onset of significant endothermic heat flow at about 200° C., as illustrated in FIG. 2. The location of the higher temperature peak varied by more than 15° C. as the heating rate was varied between 2° C./min and 10° C./min, while the location of the lower temperature feature was found to be relatively insensitive to heating rate over the same range. DSC traces were also recorded under conditions in which a sample was heated at a rate of 5° C./min to about 150° C., cooled to room temperature at a rate of 5° C./min, 30° C./min, or 40-45° C./min, and then heated again at a rate of 5° C./min. For all cooling rates, an exothermic peak was observed as the temperature was lowered, and the location of the lower temperature peak on heating a second time was unchanged from the first heating.

Without being bound to any theory of action, the sensitivity of the DSC trace to heating rate together with comparison of the DSC trace with thermogravimetric analysis data supports the inference that the crystal form of this embodiment exhibits simultaneous melting and decomposition as the temperature is scanned above the onset temperature of about 200° C. The experimental observations further support the conclusion that the lower temperature feature is characteristic of the embodiment illustrated in FIG. 2.

A crystalline monoHCl salt of the present invention has been demonstrated to be stable upon exposure to elevated temperature and humidity. For example, after storage for four weeks at 40° C. and 75% humidity in both open and closed containers and at 50° C. in a closed container, analysis by DSC shows no detectable difference and analysis by high pressure liquid chromatography (HPLC) shows no appreciable chemical degradation.

The active agent, N-{2-[4-((R)-2-hydroxy-2-phenylethylamino)phenyl]ethyl}-(R)-2-hydroxy-2-(3-formamido-4-hydroxyphenyl)ethylamine, compound 1, can be synthesized from readily available starting materials as shown in the following Scheme and further described in the Examples below. It will be appreciated that while specific process conditions (i.e. reaction temperatures, times, mole ratios of reactants, solvents, pressures, etc.) are given, other process conditions can also be used unless otherwise stated.

Scheme

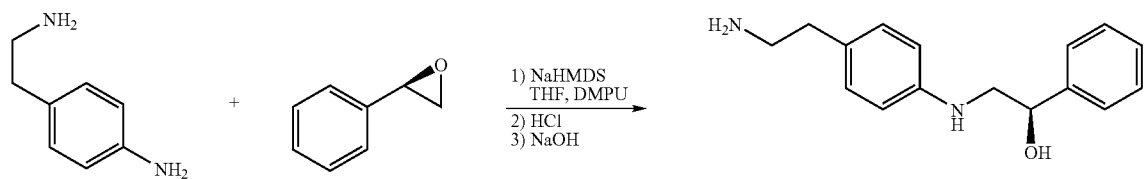

-continued

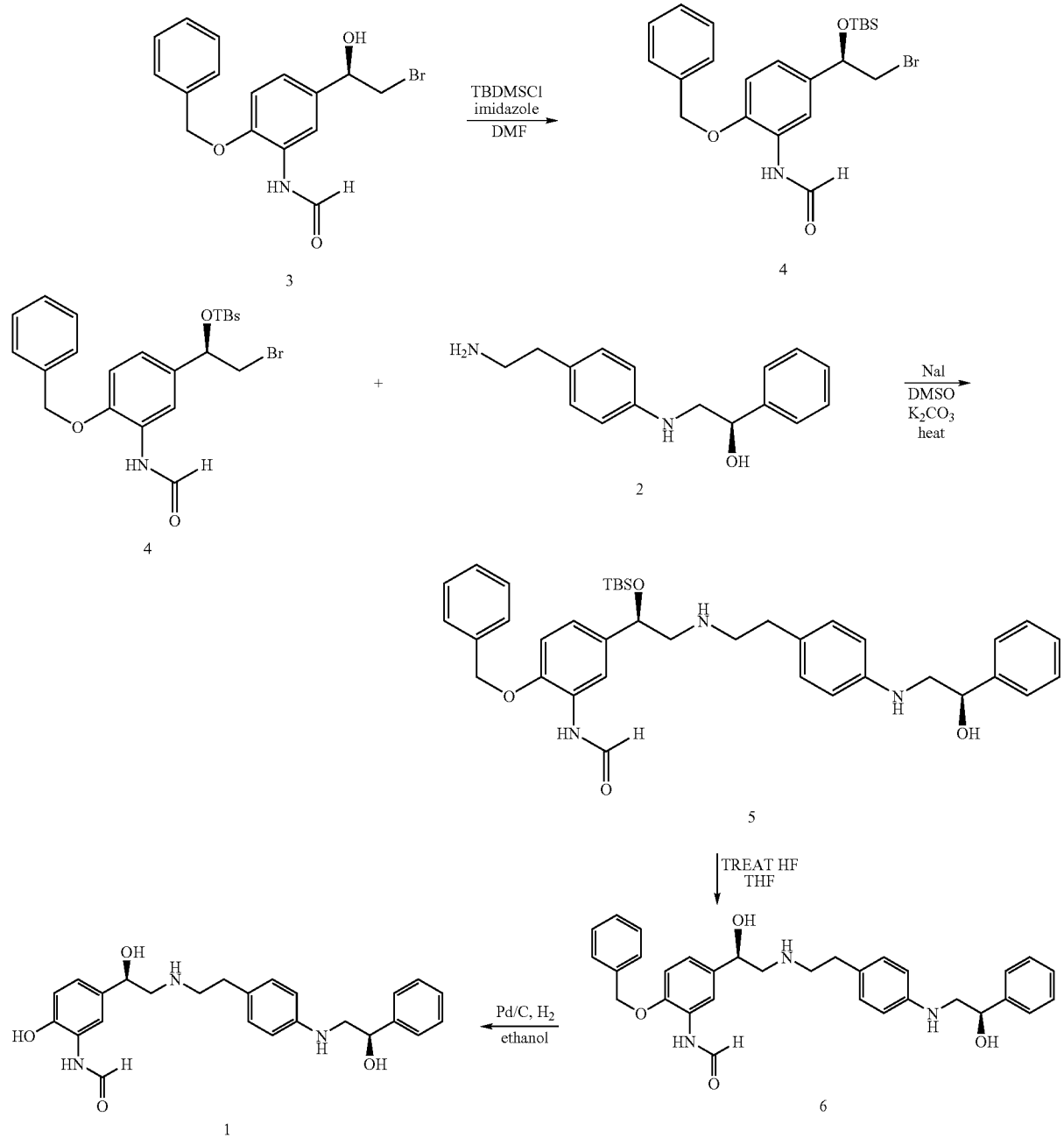

Intermediate 2 can be prepared by the coupling of 2-(4-aminophenyl)ethylamine and (R)-styrene oxide. The amine, which is optionally provided as a salt, is first reacted with between about 1 and about 1.2 equivalents of a base having a $pK_a$ value greater than about 18, in order to substantially deprotonate the 4-amino group. The (R)-styrene oxide is added to the product of the amine reaction. Useful basic compounds include sodium bis(trimethylsilyl)amide, alternatively known as sodium hexamethyldisilazane (NaHMDS), lithium diisopropyl amide, and n-butyl lithium. The reaction is preferably conducted in a solvent system including a polar aprotic solvent, such as 1,3-dimethyl-3,4,5,6-tetrahydro-2(1H)pyrimidinone (DMPU). Additional examples of aprotic polar solvents include dimethylsulfoxide, N-methyl pyrollidinone, N,N-dimethyl acetamide, tetramethylethylenediamine, and hexamethylphosphoramide.

In the process according to the present invention, no protecting groups are required on the reactants. In addition, under the present conditions, the desired regioisomer is formed in significant quantities. When a strong base capable of deprotonating the aniline is not included, the reaction gives, primarily, the undesired regioisomer resulting from endo opening of the epoxide. Inclusion of the polar aprotic solvent in the solvent system allows the anion formed from deprotonation of the aniline to remain in solution.

After aqueous extraction, the product of the coupling reaction is crystallized as the hydrochloride salt from a solvent such as isopropanol, by the addition of aqueous hydrochloric acid. The crystallization procedure efficiently separates the desired product from side products formed during the reaction. The hydrochloride salt is redissolved with 10 N aqueous sodium hydroxide to provide 2-[4-((R)-2-hydroxy-2-phenylethylamino)phenyl]ethylamine (2).

The corresponding (S) stereoisomer, 2-[4-((S)-2-hydroxy-2-phenylethylamino)phenyl]ethylamine, can be prepared by substituting (S)-styrene oxide for (R)-styrene oxide in the above procedure for the synthesis of intermediate 2.

(R)-2-Bromo-1-(3-formamido-4-benzyloxyphenyl)ethanol (3), can be prepared as described in U.S. Pat. No. 6,268,533 B1; and in R. Hett et al., *Organic Process Research and Development*, 1998, 2, 96-99. Intermediate 3 can also be prepared using procedures similar to those described by Hong et al., *Tetrahedron Lett.*, 1994, 35, 6631; or similar to those described in U.S. Pat. No. 5,495,054. Intermediate 4,2-bromo-(R)-1-tert-butyldimethylsiloxy-1-(3-formamido-4-benzyloxyphenyl)ethane, including the protecting group tert-butydimethylsilyl (TBS) at the hydroxyl position of 3 can be formed by the addition of tert-butydimethylsilylchloride (TBDMSCl) and imidazole to intermediate 3, dissolved in dimethylformamide (DMF).

Intermediates 2 and 4 are coupled, using dimethylsulfoxide (DMSO) as the solvent, by adding potassium carbonate and sodium iodide and heating to about 140° C. to form intermediate 5. N-{2-[4-((R)-2-hydroxy-2-phenylethylamino)phenyl]ethyl}-(R)-2-tert-butyldimethylsiloxy-2-(3-formamido-4-benzyloxyphenyl)ethylamine. The TBS protecting group is removed from 5, dissolved in tetrahydrofuran (THF), by addition of triethylamine trihydrofluoride (TREAT HF), giving intermediate 6, N-{2-[4-((R)-2-hydroxy-2-phenylethylamino)phenyl]ethyl}-(R)-2-hydroxy-2-(3-formamido-4-benzyloxyphenyl)ethylamine, upon isolation. The benzyl protecting group is removed from intermediate 6 by catalytic hydrogenolysis, using palladium on activated carbon, providing the active compound 1.

A crystalline monohydrochloride salt of the present invention can be formed by the addition of between about 0.9 and about 1 molar equivalent of aqueous hydrochloric acid to the active compound 1 dissolved in a polar solvent. Suitable polar solvents include isopropanol and water. To induce crystallization, preferably the solution from which the monoHCl product is crystallized includes isopropanol and water in a ratio of isopropanol to water of from about 4:1 to about 10:1, volume to volume. More preferably, the ratio of isopropanol to water is from about 4:1 to about 7:1, volume to volume. The water component can be present in the polar solvent or can be introduced as aqueous hydrochloric acid. Preferably the ratio of total solvent to free base material is from about 15:1 to about 50:1, volume (mL) to weight (g). Optionally, the mixture of compound 1 and polar solvent can be heated to dissolve the freebase and the resulting mixture cooled back to room temperature before addition of hydrochloric acid.

For example, a crystalline monoHCl salt can be formed by dissolving compound 1 in isopropanol at a temperature of between about 40° C. and about 60° C., cooling to room temperature, adding aqueous hydrochloric acid, and stirring during crystallization. The crystalline product can be isolated by filtration and dried under vacuum.

Alternatively, a crystalline monohydrochloride salt can be formed from the free base by the addition of a molar excess of an aqueous solution of an inorganic chloride at a pH of between about 5 and about 6 to the active compound 1 dissolved in a polar, water soluble solvent. A suitable source of chloride ions at relatively high pH is ammonium chloride and a suitable polar solvent is isopropanol. For example the crystalline monoHCl salt can be formed by dissolving compound 1 in isopropanol, adding aqueous ammonium chloride, and allowing the solution to stand overnight at room temperature. The crystalline product can be isolated by filtration and dried.

Using another alternative process, a crystalline monoHCl salt can be formed from the protected intermediate 5. As described in Example 13 below, according to this alternative process, intermediate 5 is first contacted with a weak acid, for example, acetic acid, to effect selective protonation and then contacted with a source of chloride ions, for example, sodium chloride, to effect anion exchange. The protecting groups are removed sequentially. The TBS protecting group is removed, for example using cesium fluoride in an organic solvent, providing the monoHCl salt of intermediate 6, and then the benzyl protecting group is removed, for example, by hydrogenation using a palladium or platinum catalyst. A monohydrochloride salt of compound 1 may be obtained in crystalline form by precipitation from an aqueous organic solution.

In yet another alternative method, a crystalline monochloride salt of the present invention can be formed from a water slurry of the corresponding dihydrochloride salt. To form the slurry, water is added to a vial of the diHCl salt of compound 1 and the resulting product is stirred for more than 48 hours. Optionally, the pH of the slurry can be adjusted to between about 5 and about 6 before stirring. The crystalline monoHCl product can be isolated from the slurry by filtration and dried.

Further, it has been discovered that a crystalline monohydrochloride salt of the present invention, can be obtained by recrystallizing a hydrochloride salt of compound 1 having between 1 and 2 equivalents of chlorine per mole of compound 1. The monohydrochloride salt can be formed by dissolving a hydrochloride salt of compound 1 having between 1 and 2 equivalents of chlorine per mole of free base in a polar solvent to form a first solution and adding a polar solvent to form a second solution from which the salt form crystallizes. As described in Examples 9 and 10 below, the monohydrochloride salt was produced by dissolving a hydrochloride salt having 1.52 equivalents of HCl per mole of free base in isopropanol and water at elevated temperature, diluting with isopropanol, and cooling to room temperature with stirring.

A procedure for the formation of the dihydrochloride salt of the present active agent is as follows. At least two equivalents of hydrochloric acid is added to compound 1 dissolved in a polar solvent. To induce crystallization, preferably the solution from which the diHCl product is crystallized includes isopropanol and water in a ratio of isopropanol to water of from about 4:1 to about 10:1, volume to volume. More preferably, the ratio of isopropanol to water is from about 4:1 to about 7:1, volume to volume. The water component can be present in the polar solvent or can be introduced as aqueous hydrochloric acid. Preferably the ratio of total solvent to free base material is from about 15:1 to about 50:1, volume (mL) to weight (g). Optionally, the mixture of compound 1 and polar solvent can be heated to dissolve the freebase and the resulting mixture cooled back to room temperature before addition of hydrochloric acid.

For example, the crystalline diHCl salt can be formed by dissolving compound 1 in isopropanol at a temperature of between about 40° C. and about 60° C., cooling to room temperature, adding aqueous hydrochloric acid, and stirring during crystallization. The crystalline product can be isolated by filtration and dried under vacuum.

Optionally, the crystalline diHCl salt can be recrystallized by redissolving the crystalline salt in a polar solvent as described above. To ensure that the recrystallized product has two equivalents of HCl per mole of free base, particularly when preparing the product at greater than gram scale, hydrochloric acid can be included in the polar solvent. In these preparations, between about 0.5 and about 1.5, for example, about 1 equivalent of HCl per mole of free base is usefully included in the polar solvent.

As illustrated in Example 6b below, the crystalline diHCl salt can be recrystallized by dissolving in a mixture of isopropanol and water at elevated temperature, diluting with isopropanol, and cooling to room temperature with stirring. The diHCl product can be isolated by filtration and dried under vacuum.

Pharmaceutical Compositions

A crystalline form of the monoHCl salt of the present invention is advantageously used to prepare pharmaceutical compositions formulated for administration by inhalation. Inhalation is an effective means for delivering an agent directly to the respiratory tract. There are three general types of pharmaceutical inhalation devices: nebulizer inhalers, dry powder inhalers (DPI), and metered-dose inhalers (MDI). Conventional nebulizer devices produce a stream of high velocity air that causes a therapeutic agent to spray as a mist which is carried into the patient's respiratory tract. The therapeutic agent is formulated in a liquid form such as a solution or a suspension of micronized particles of respirable size, where micronized is typically defined as having about 90% or more of the particles with a diameter of less than about 10 μm. Suitable nebulizer devices are provided commercially, for example, by PARI GmbH (Starnberg, Germany). Other nebulizer devices have been disclosed, for example, in U.S. Pat. No. 6,123,068. The present crystalline monoHCl salt can be formulated for use in a conventional nebulizer device as an aqueous solution at a concentration of between about 0.05 μg/mL and about 10 mg/mL of the free base active agent, compound 1.

DPI's typically administer a therapeutic agent in the form of a free flowing powder that can be dispersed in a patient's air-stream during inspiration. Alternative DPI devices which use an external energy source are also being developed. In order to achieve a free flowing powder, the therapeutic agent can be formulated with a suitable excipient (e.g., lactose). A dry powder formulation can be made, for example, by combining dry lactose having a particle size between about 1 μm and 100 μm with micronized particles of the monoHCl salt of compound 1 and dry blending. Alternatively, the agent can be formulated without excipients. The formulation is loaded into a dry powder dispenser, or into inhalation cartridges or capsules for use with a dry powder delivery device.

Examples of DPI delivery devices provided commercially include Diskhaler (GlaxoSmithKline, Research Triangle Park, N.C.) (see, e.g., U.S. Pat. No. 5,035,237); Diskus (GlaxoSmithKline) (see, e.g., U.S. Pat. No. 6,378,519; Turbuhaler (AstraZeneca, Wilmington, Del.) (see, e.g., U.S. Pat. No. 4,524,769); and Rotahaler (GlaxoSmithKline) (see, e.g., U.S. Pat. No. 4,353,365). Further examples of suitable DPI devices are described in U.S. Pat. Nos. 5,415,162, 5,239,993, and 5,715,810 and references therein.

MDI's typically discharge a measured amount of therapeutic agent using compressed propellant gas. Formulations for MDI administration include a solution or suspension of active ingredient in a liquefied propellant. While chlorofluorocarbons, such as $CCl_3F$, conventionally have been used as propellants, due to concerns regarding adverse affects of such agents on the ozone layer, formulations using hydrofluoroalklanes (HFA), such as 1,1,1,2-tetrafluoroethane (HFA 134a) and 1,1,1,2,3,3,3-heptafluoro-n-propane, (HFA 227) have been developed. Additional components of HFA formulations for MDI administration include co-solvents, such as ethanol, pentane, or minor amounts of water; and surfactants, such as sorbitan trioleate, oleic acid, lecithin, and glycerin. (See, for example, U.S. Pat. No. 5,225,183, EP 0717987 A2, and WO 92/22286).

Thus, a suitable formulation for MDI administration can include from about 0.001% to about 2% by weight of the present crystalline form, from about 0% to about 20% by weight ethanol, and from about 0% to about 5% by weight surfactant, with the remainder being the HFA propellant. In one approach, to prepare the formulation, chilled or pressurized hydrofluoroalkane is added to a vial containing the present crystalline form, ethanol (if present) and the surfactant (if present). To prepare a suspension, the pharmaceutical salt is provided as micronized particles. The formulation is loaded into an aerosol canister, which forms a portion of an MDI device. Examples of MDI devices developed specifically for use with HFA propellants are provided in U.S. Pat. Nos. 6,006,745 and 6,143,227.

In an alternative preparation, a suspension formulation is prepared by spray drying a coating of surfactant on micronized particles of the present crystalline material. (See, for example, WO 99/53901 and WO 00/61108). For additional examples of processes of preparing respirable particles, and formulations and devices suitable for inhalation dosing see U.S. Pat. Nos. 6,268,533, 5,983,956, 5,874,063, and 6,221,398, and WO 99/55319 and WO 00/30614.

The present active agent, compound 1, is useful as a $\beta_2$ adrenergic receptor agonist and therefore is useful for treating medical diseases or conditions mediated by $\beta_2$ adrenergic receptors or associated with $\beta_2$ adrenergic receptor activity in a mammal, i.e. medical conditions which are ameliorated by treatment with a $\beta_2$ adrenergic receptor agonist. Such medical conditions include but are not limited to a pulmonary disease, such as asthma or chronic obstructive pulmonary disease, pre-term labor, a neurological disorder, a cardiac disorder, or inflammation.

The present active agent, compound 1, is effective over a wide dosage range and is generally administered in a therapeutically effective amount. It will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses of the therapeutic agent for inhalation administration are in the general range of from about 0.05 μg/day to about 1000 μg/day, preferably from about 0.1 μg/day to about 500 μg/day.

A compound can be administered in a periodic dose: weekly, multiple times per week, daily, or multiple doses per day. The treatment regimen may require administration over extended periods of time, for example, for several weeks or months, or the treatment regimen may require chronic administration. Suitable doses for oral administration are in the general range of from about 0.05 μg/day to about 100 mg/day, preferably from about 0.5 μg/day to about 1000 μg/day.

The invention thus provides a method of treating a mammal having a disease or condition associated with $\beta_2$ adrenergic receptor activity, the method comprising administering to the mammal a therapeutically effective amount of the monohydrochloride salt of compound 1 or of a pharmaceutical composition comprising the monohydrochloride salt of compound 1.

The present active agent can also be co-administered with one or more other therapeutic agents. For example, the present agent can be administered in combination with one or more therapeutic agents selected from anti-inflammatory agents (e.g. corticosteroids and non-steroidal anti-inflammatory agents (NSAIDs), antichlolinergic agents (particularly muscarinic receptor antagonists), other $\beta_2$ adrenergic receptor agonists, antiinfective agents (e.g. antibiotics or antivirals) or antihistamines. The invention thus provides, in a further aspect, a combination comprising the monohydrochloride salt of compound 1 together with one or more therapeutic agent, for example, an anti-inflammatory agent, an antichlolinergic agent, another $\beta_2$ adrenergic receptor agonist, an antiinfective agent or an antihistamine.

The other therapeutic agents can be used in the form of pharmaceutically acceptable salts or solvates. As appropriate, the other therapeutic agents can be used as optically pure stereoisomers.

Suitable anti-inflammatory agents include corticosteroids and NSAIDs. Suitable corticosteroids which may be used in combination with the compounds of the invention are those oral and inhaled corticosteroids and their pro-drugs which have anti-inflammatory activity. Examples include methyl prednisolone, prednisolone, dexamethasone, fluticasone propionate, 6α,9α-difluoro-17α-[(2-furanylcarbonyl)oxy]-11β-hydroxy-16α-methyl-3-oxo-androsta-1,4-diene-17β-carbothioic acid S-fluoromethyl ester, 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester, beclomethasone esters (e.g. the 17-propionate ester or the 17,21-dipropionate ester), budesonide, flunisolide, mometasone esters (e.g. the furoate ester), triamcinolone acetonide, rofleponide, ciclesonide, butixocort propionate, RPR-106541, and ST-126. Preferred corticosteroids include fluticasone propionate, 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester and 6α,9α-difluoro-17α-[(2-furanylcarbonyl)oxy]-11β-hydroxy-16α-methyl-3-oxo-androsta-1,4-diene-17β-carbothioic acid S-fluoromethyl ester, more preferably 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

Suitable NSAIDs include sodium cromoglycate; nedocromil sodium; phosphodiesterase (PDE) inhibitors (e.g. theophylline, PDE4 inhibitors or mixed PDE3/PDE4 inhibitors); leukotriene antagonists (e.g. monteleukast); inhibitors of leukotriene synthesis; iNOS inhibitors; protease inhibitors, such as tryptase and elastase inhibitors; beta-2 integrin antagonists and adenosine receptor agonists or antagonists (e.g. adenosine 2a agonists); cytokine antagonists (e.g. chemokine antagonists such as, an interleukin antibody (αIL antibody), specifically, an αIL-4 therapy, an αIL-13 therapy, or a combination thereof); or inhibitors of cytokine synthesis. Suitable other $\beta_2$-adrenoreceptor agonists include salmeterol (e.g. as the xinafoate), salbutamol (e.g. as the sulphate or the free base), formoterol (e.g. as the fumarate), fenoterol or terbutaline and salts thereof.

Also of interest is use of the present active agent in combination with a phosphodiesterase 4 (PDE4) inhibitor or a mixed PDE3/PDE4 inhibitor. The PDE4-specific inhibitor useful in this aspect of the invention may be any compound that is known to inhibit the PDE4 enzyme or which is discovered to act as a PDE4 inhibitor, and which are only PDE4 inhibitors. Preferred compounds are cis 4-cyano-4-(3-cyclopentyloxy-4-methoxyphenyl)cyclohexan-1-carboxylic acid, 2-carbomethoxy-4-cyano-4-(3-cyclopropylmethoxy-4-difluoromethoxyphenyl)cyclohexan-1-one and cis-[4-cyano-4-(3-cyclopropylmethoxy-4-difluoromethoxyphenyl)cyclohexan-1-ol].

Other compounds of interest include:

Compounds set out in U.S. Pat. No. 5,552,438 issued Sep. 3, 1996; this patent and the compounds it discloses are incorporated herein by reference. The compound of particular interest, which is disclosed in U.S. Pat. No. 5,552,438, is cis-4-cyano-4-[3-(cyclopentyloxy)-4-methoxyphenyl]cyclohexane-1-carboxylic acid (also known as cilomalast) and its salts, esters, pro-drugs or physical forms;

AWD-12-281 from elbion (Hofgen, N. et al. 15th EFMC Int Symp Med Chem (Sep. 6-10, Edinburgh) 1998, Abst P.98; CAS reference No. 247584020-9); a 9-benzyladenine derivative nominated NCS-613 (INSERM); D-4418 from Chiroscience and Schering-Plough; a benzodiazepine PDE4 inhibitor identified as CI-1018 (PD-168787) and attributed to Pfizer; a benzodioxole derivative disclosed by Kyowa Hakko in WO99/16766; K-34 from Kyowa Hakko; V-11294A from Napp (Landells, L. J. et al. Eur Resp J [Annu Cong Eur Resp Soc (Sep. 19-23, Geneva) 1998] 1998, 12 (Suppl. 28): Abst P2393); roflumilast (CAS reference No 162401-32-3) and a pthalazinone (WO99/47505, the disclosure of which is hereby incorporated by reference) from Byk-Gulden; Pumafentrine, (−)-p-[(4aR*,10bS*)-9-ethoxy-1,2,3,4,4a,10b-hexahydro-8-methoxy-2-methylbenzo[c][1,6]naphthyridin-6-yl]-N,N-diisopropylbenzamide which is a mixed PDE3/PDE4 inhibitor which has been prepared and published on by Byk-Gulden, now Altana; arofylline under development by Almirall-Prodesfarma; VM554/UM565 from Vernalis; or T-440 (Tanabe Seiyaku; Fuji, K. et al. J Pharmacol Exp Ther, 1998, 284(1): 162), and T2585.

Other possible PDE-4 and mixed PDE3/PDE4 inhibitors include those listed in WO01/13953, the disclosure of which is hereby incorporated by reference.

Suitable anticholinergic agents are those compounds that act as antagonists at the muscarinic receptor, in particular those compounds which are antagonists of the $M_1$, $M_2$, or $M_3$ receptors, or of combinations thereof. Exemplary compounds include the alkaloids of the belladonna plants as illustrated by the likes of atropine, scopolamine, homatropine, hyoscyamine; these compounds are normally administered as a salt, being tertiary amines. These drugs, particularly the salt forms, are readily available from a number of commercial sources or can be made or prepared from literature data via, to wit:

Atropine—CAS-51-55-8 or CAS-51-48-1 (anhydrous form), atropine sulfate—CAS-5908-99-6; atropine oxide—CAS-4438-22-6 or its HCl salt—CAS-4574-60-1 and methylatropine nitrate—CAS-52-88-0.

Homatropine—CAS-87-00-3, hydrobromide salt—CAS-51-56-9, methylbromide salt—CAS-80-49-9.

Hyoscyamine (d, l)—CAS-101-31-5, hydrobromide salt—CAS-306-03-6 and sulfate salt—CAS-6835-16-1.

Scopolamine—CAS-51-34-3, hydrobromide salt—CAS-6533-68-2, methylbromide salt—CAS-155-41-9.

Preferred anticholinergics include ipratropium (e.g. as the bromide), sold under the name Atrovent, oxitropium (e.g. as the bromide) and tiotropium (e.g. as the bromide) (CAS-13940448-1). Also of interest are: methantheline (CAS-53-46-3), propantheline bromide (CAS-50-34-9), anisotropine methyl bromide or Valpin 50 (CAS-80-50-2), clidinium bromide (Quarzan, CAS-3485-62-9), copyrrolate (Robinul), isopropamide iodide (CAS-71-81-8), mepenzolate bromide (U.S. Pat. No. 2,918,408), tridihexethyl chloride (Pathilone, CAS-4310-35-4), and hexocyclium methylsulfate (Tral, CAS-115-63-9). See also cyclopentolate hydrochloride (CAS-5870-29-1), tropicamide (CAS-1508-75-4), trihexyphenidyl hydrochloride (CAS-144-11-6), pirenzepine (CAS-29868-97-1), telenzepine (CAS-80880-90-9), AF-DX 116, or methoctramine, and the compounds disclosed in WO01/04118, the disclosure of which is hereby incorporated by reference.

Suitable antihistamines (also referred to as $H_1$-receptor antagonists) include any one or more of the numerous antagonists known which inhibit $H_1$-receptors, and are safe for human use. All are reversible, competitive inhibitors of the interaction of histamine with $H_1$-receptors. The majority of these inhibitors, mostly first generation antagonists, are characterized, based on their core structures, as ethanolamines, ethylenediamines, and alkylamines. In addition, other first generation antihistamines include those which can be characterized as based on piperizine and phenothiazines. Second generation antagonists, which are non-sedating, have a similar structure-activity relationship in that they retain the core ethylene group (the alkylamines) or mimic a tertiary amine group with piperizine or piperidine. Exemplary antagonists are as follows:

Ethanolamines: carbinoxamine maleate, clemastine fumarate, diphenylhydramine hydrochloride, and dimenhydrinate.

Ethylenediamines: pyrilamine amleate, tripelennamine HCl, and tripelennamine citrate.

Alkylamines: chlorpheniramine and its salts such as the maleate salt, and acrivastine.

Piperazines: hydroxyzine HCl, hydroxyzine pamoate, cyclizine HCl, cyclizine lactate, meclizine HCl, and cetirizine HCl.

Piperidines: Astemizole, levocabastine HCl, loratadine or its descarboethoxy analogue, and terfenadine and fexofenadine hydrochloride or another pharmaceutically acceptable salt.

Azelastine hydrochloride is yet another $H_1$ receptor antagonist which may be used in combination with the present active agent.

Examples of preferred anti-histamines include methapyrilene and loratadine.

The invention thus provides, in a further aspect, a combination comprising the monohydrochloride salt of compound 1 and a corticosteroid.

In particular, the invention provides combinations comprising the monohydrochloride salt of compound 1 and fluticasone propionate; the monohydrochloride salt of compound 1 and 6α,9α-difluoro-17α-[(2-furanylcarbonyl)oxy]-11β-hydroxy-16α-methyl-3-oxo-androsta-1,4-diene-17β-carbothioic acid S-fluoromethyl ester; and the monohydrochloride salt of compound 1 and 6α,9α-difluoro-11β-hydroxy-16α-methyl-3-oxo-17α-propionyloxy-androsta-1,4-diene-17β-carbothioic acid S-(2-oxo-tetrahydro-furan-3S-yl) ester.

The invention thus provides, in a further aspect, a combination comprising the monohydrochloride salt of compound 1 and a PDE4 inhibitor.

The invention thus provides, in a further aspect, a combination comprising the monohydrochloride salt of compound 1 and an anticholinergic agent.

The invention thus provides, in a further aspect, a combination comprising the monohydrochloride salt of compound 1 and an antihistamine.

The invention thus provides, in a further aspect, a combination comprising the monohydrochloride salt of compound 1 together with a PDE4 inhibitor and a corticosteroid.

The invention thus provides, in a further aspect, a combination comprising the monohydrochloride salt of compound 1 together with an anticholinergic agent and a corticosteroid.

Accordingly, the pharmaceutical compositions of the invention can optionally comprise combinations of the present monohydrochloride salt of compound 1 with one or more other therapeutic agents, as described above.

The individual compounds of such combinations may be administered either sequentially or simultaneously in separate or combined pharmaceutical formulations. Appropriate doses of known therapeutic agents will be readily appreciated by those skilled in the art.

According to a further aspect, the invention provides a method of treating a disease or condition associated with $\beta_2$ adrenergic receptor activity in a mammal, comprising administering to the mammal a therapeutically effective amount of a combination of the present monohydrochloride salt of compound 1 with one or more other therapeutic agents.

Further, the present crystalline salt, potentially can be formulated for other forms of administration, such as oral or parenteral administration. The salt can be admixed with conventional pharmaceutical carriers and excipients and used in the form of powders, tablets, capsules, elixirs, suspensions, syrups, wafers, and the like. Such pharmaceutical compositions will contain from about 0.05 to about 90% by weight of the active compound, and more generally from about 0.1 to about 30%. Additional suitable pharmaceutical carriers for formulation of the crystalline salt of the present invention can be found in *Remington: The Science and Practice of Pharmacy*, 20*th Edition*, Lippincott Williams & Wilkins, Philadelphia, Pa., 2000.

The following non-limiting examples illustrate representative pharmaceutical compositions of the invention, where active ingredient is defined as crystalline N-{2-[4-((R)-2-hydroxy-2-phenylethylamino)phenyl]ethyl}-(R)-2-hydroxy-2-(3-formamido-4-hydroxyphenyl)ethylamine monohydrochloride.

Formulation Example A

This example illustrates the preparation of a representative pharmaceutical composition for oral administration of a crystalline monoHCl salt of this invention:

| Ingredients | Quantity per tablet, (mg) |
| --- | --- |
| Active Ingredient | 1 |
| Lactose, spray-dried | 148 |
| Magnesium stearate | 2 |

The above ingredients are mixed and introduced into a hard-shell gelatin capsule.

Formulation Example B

This example illustrates the preparation of another representative pharmaceutical composition for oral administration of a crystalline monoHCl salt of this invention:

| Ingredients | Quantity per tablet, (mg) |
| --- | --- |
| Active Ingredient | 1 |
| Cornstarch | 50 |
| Lactose | 145 |
| Magnesium stearate | 5 |

The above ingredients are mixed intimately and pressed into single scored tablets.

Formulation Example C

This example illustrates the preparation of a representative pharmaceutical composition for oral administration of a crystalline monoHCl salt of this invention.

An oral suspension is prepared having the following composition.

| Ingredients | | |
|---|---|---|
| Active Ingredient | 3 | mg |
| Fumaric acid | 0.5 | g |
| Sodium chloride | 2.0 | g |
| Methyl paraben | 0.1 | g |
| Granulated sugar | 25.5 | g |
| Sorbitol (70% solution) | 12.85 | g |
| Veegum K (Vanderbilt Co.) | 1.0 | g |
| Flavoring | 0.035 | mL |
| Colorings | 0.5 | mg |
| Distilled water | q.s. to 100 | mL |

Formulation Example D

This example illustrates the preparation of a representative pharmaceutical composition containing a crystalline mono-HCl salt of this invention.

An injectable preparation buffered to a pH of 4 is prepared having the following composition:

| Ingredients | |
|---|---|
| Active Ingredient | 0.1 mg |
| Sodium Acetate Buffer Solution (0.4 M) | 2.0 mL |
| HCl (1 N) | q.s. to pH 4 |
| Water (distilled, sterile) | q.s. to 20 mL |

Formulation Example E

This example illustrates the preparation of a representative pharmaceutical composition for injection using a crystalline monoHCl salt of this invention.

A reconstituted solution is prepared by adding 20 mL of sterile water to 1 mg of the compound of this invention. Before use, the solution is then diluted with 200 mL of an intravenous fluid that is compatible with the active compound. Such fluids are chosen from 5% dextrose solution, 0.9% sodium chloride, or a mixture of 5% dextrose and 0.9% sodium chloride. Other examples are lactated Ringer's injection, lactated Ringer's plus 5% dextrose injection, Normosol-M and 5% dextrose, Isolyte E, and acylated Ringer's injection.

Formulation Example F

This example illustrates the preparation of a representative pharmaceutical composition for topical application of a crystalline monoHCl salt of this invention.

| Ingredients | grams |
|---|---|
| Active ingredient | 0.2-10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients, and water then added q.s. 100 g.

Formulation Example G

This example illustrates the preparation of a representative pharmaceutical composition containing a compound of the invention.

An aqueous aerosol formulation for use in a nebulizer is prepared by dissolving 0.1 mg of the monoHCl salt of the invention in 1 mL of a 0.9% sodium chloride solution acidified with citric acid. The mixture is stirred and sonicated until the active salt is dissolved. The pH of the solution is adjusted to a value in the range of from 3 to 8 by the slow addition of NaOH.

Formulation Example H

This example illustrates the preparation of a dry powder formulation containing a monoHCl salt of the invention for use in inhalation cartridges.

Inhalation cartridges are filled with a pharmaceutical composition having the following ingredients:

| Ingredients | mg/cartridge |
|---|---|
| Active ingredient | 0.2 |
| Lactose | 25 |

The active ingredient is micronized prior to blending with lactose. The contents of the cartridges are administered using a powder inhaler.

Formulation Example I

This example illustrates the preparation of a dry powder formulation containing a crystalline monoHCl salt of this invention for use in a dry powder inhalation device.

A pharmaceutical composition is prepared having a bulk formulation ratio of micronized active ingredient to lactose of 1:200. The composition is packed into a dry powder inhalation device capable of delivering between about 10 and about 100 μg of active drug ingredient per dose.

Formulation Example J

This example illustrates the preparation of a formulation containing a crystalline monoHCl salt of this invention for use in a metered dose inhaler.

A suspension containing 5% active ingredient, 0.5% lecithin, and 0.5% trehalose is prepared by dispersing 5 g of active compound as micronized particles with mean size less than 10 μm in a colloidal solution formed from 0.5 g of trehalose and 0.5 g of lecithin dissolved in 100 mL of demineralized water. The suspension is spray dried and the resulting material is micronized to particles having a mean diameter less than 1.5 μm. The particles are loaded into canisters with pressurized 1,1,1,2-tetrafluoroethane.

Formulation Example K

This example illustrates the preparation of a formulation containing a crystalline monoHCl salt of this invention for use in a metered dose inhaler.

A suspension containing 5% active ingredient and 0.1% lecithin is prepared by dispersing 10 g of active compound as micronized particles with mean size less than 10 μm in a solution formed from 0.2 g of lecithin dissolved in 200 mL of demineralized water. The suspension is spray dried and the resulting material is micronized to particles having a mean diameter less than 1.5 μm. The particles are loaded into canisters with pressurized 1,1,1,2,3,3,3-heptafluoro-n-propane.

The following exemplify the preparation of N-{2-[4-((R)-2-hydroxy-2-phenylethylamino)phenyl]ethyl}-(R)-2-hydroxy-2-(3-formamido-4-hydroxyphenyl)ethylamine, compound 1; preparation, characterization, and stability testing of the monoHCl salt of compound 1; and preparation of the diHCl salt of compound 1.

Example 1

Synthesis of 2-[4-((R)-2-hydroxy-2-phenylethylamino)phenyl]ethylamine (2)

To a 1000 mL 3-neck flask was added 10 g (74 mmol) of 2-(4-aminophenyl)ethylamine and 15 mL of 1,3-dimethyl-3,4,5,6-tetrahydro-2(1H)pyrimdinone (DMPU). The reaction flask was fitted with an overhead stirrer, a 125 mL addition funnel and a thermometer. The reaction flask was purged with nitrogen and placed in a cold water bath. The addition funnel was charged with 83 mL (83 mmol) of 1.0 M sodium bis(trimethylsilyl)amide in tetrahydrofuran. The sodium bis(trimethylsilyl)amide solution was added dropwise over 30 min with vigorous stirring. The addition funnel was removed and replaced with a rubber septum. (R)-styrene oxide (8.4 mL, 74 mmol) was added dropwise by syringe over 10 minutes. The rate of addition was controlled to maintain a temperature below 35° C. After 1 h, the reaction was quenched by dropwise addition of 88 mL water. The reaction mixture was transferred to a separatory funnel, diluted with 56 mL isopropyl acetate and washed with 84 mL saturated aqueous sodium chloride. The organic layer was washed a second time with a mixture of 84 mL water and 84 mL saturated aqueous sodium chloride and finally with 84 mL saturated aqueous sodium chloride. The organic layer was concentrated under vacuum. The residue was twice reconcentrated from isopropanol (55 mL portions) and then redissolved in isopropanol (235 mL) and heated to 70° C. with stirring. Concentrated hydrochloric acid (13.2 mL, 160 mmol) was added over two minutes. The mixture was allowed to cool to room temperature and stirred for 14 h. The precipitated product was isolated by filtration and washed with isopropanol and isopropyl acetate. The product was dried under vacuum for 3 h and then dissolved in 56 mL water and transferred to a separatory funnel. Isopropyl acetate (56 mL) and 10 N aqueous sodium hydroxide (19 mL, 190 mmol) were added. The separatory funnel was shaken and the phases separated. The organic layer was dried over sodium sulfate and concentrated to afford the product 2 as an orange-brown oil (11 g, 44 mmol, 59%). m/z: [M+H$^+$] calcd for $C_{16}H_{20}N_2O$ 257.2. found 257.2.

Example 2

Synthesis of 2-bromo-(R)-1-tert-butyldimethylsiloxy-1-(3-formamido-4-benzyloxyphenyl)ethane (4)

(R)-2-Bromo-1-(3-formamido-4-benzyloxyphenyl)ethanol (intermediate 3) (9.9 g, 28 mmol) was dissolved in 36 mL dimethylformamide. Imidazole (2.3 g, 34 mmol) and t-butyldimethylsilylchloride (4.7 g, 31 mmol) were added. The solution was stirred under nitrogen atmosphere for 72 h. Additional imidazole (0.39 g, 5.7 mmol) and t-butyldimethylsilylchloride (0.64 g, 4.3 mmol) were added and the reaction was stirred for an additional 20 h. The reaction was diluted with a mixture of isopropyl acetate (53 mL) and hexanes (27 mL) and transferred to a separatory funnel. The organic layer was twice washed with a mixture of water (27 mL) and saturated aqueous sodium chloride (27 mL) followed by a final wash with saturated aqueous sodium chloride (27 mL). The organic layer was dried over sodium sulfate. Silica gel (23.6 g) and hexanes (27 mL) were added and the suspension was stirred for 10 minutes. The solids were removed by filtration and the filtrate concentrated under vacuum. The residue was crystallized from hexanes (45 mL) to afford 8.85 g (19 mmol, 68%) of intermediate 4 as a white solid. m/z: [M+H$^+$] calcd for $C_{22}H_{30}NO_3SiBr$ 464.1, 466.1. found 464.2, 466.4.

Example 3

Synthesis of N-{2-[4-((R)-2-hydroxy-2-phenylethylamino)phenyl]ethyl}-(R)-2-tert-butyldimethylsiloxy-2-(3-formamido-4-benzyloxyphenyl)ethylamine (5)

Intermediate 4 (5.0 g, 11 mmol), intermediate 2 (3.5 g, 14 mmol), and dimethylsulfoxide (10 mL) were combined in a 100 mL round bottom flask and stirred to form a homogeneous solution. Potassium carbonate (6.0 g, 43 mmol) and sodium iodide (1.7 g, 11 mmol) were added and the reaction mixture was heated to 140° C. The reaction mixture was maintained at 140° C. for 10 min, then cooled to room temperature and diluted with water (24 mL) and isopropyl acetate (28 mL). The reaction was stirred until all solids dissolved and then transferred to a separatory funnel. The organic layer was washed with water (17 mL) followed by acetate buffer (5% v/v acetic acid, 12% w/v sodium acetate trihydrate in water, 18 ml) followed by sodium bicarbonate solution (5% w/v in water, 17 mL) followed by saturated aqueous sodium chloride (17 mL). The organic layer was dried over sodium sulfate and concentrated to afford intermediate 5 as a brown gelatinous solid (7.0 g, 11 mmol, >99%). m/z: [M+H$^+$] calcd for $C_{38}H_{49}N_3O_4Si$ 640.4. found 640.6.

Example 4

Synthesis of N-{2-[4-((R)-2-hydroxy-2-phenylethylamino)phenyl]ethyl}-(R)-2-hydroxy-2-(3-formamido-4-benzyloxyphenyl)ethylamine (6)

Intermediate 5 (5.2 g, 8.1 mmol) was dissolved in tetrahydrofuran (26 mL) and triethylamine trihydrofluoride (1.4 mL, 8.6 mmol) was added. The solution was stirred for 20 h. The reaction was quenched by addition of water (7.6 mL) followed by 10.0 N sodium hydroxide (3.8 mL, 38 mmol). After 3 min, the reaction was diluted with isopropyl acetate (20 mL) and transferred to a separatory funnel. The mixture was shaken and the biphasic mixture was filtered through celite to remove undissolved solids. The filtrate was returned to a separatory funnel and the phases were separated. The organic layer was washed with a mixture of 9 mL water and 9 mL saturated aqueous sodium chloride followed by 15 mL of saturated aqueous sodium chloride. The organic layer was dried over sodium sulfate and concentrated to afford the product 6 as a brown gelatinous solid (4.2 g, 8.0 mmol, 99%). m/z: [M+H$^+$] calcd for $C_{32}H_{35}N_3O_4$ 526.3. found 526.4.

Example 5

Synthesis of N-{2-[4-((R)-2-hydroxy-2-phenylethylamino)phenyl]ethyl}-(R)-2-hydroxy-2-(3-formamido-4-hydroxyphenyl)ethylamine (1)

Intermediate 6 (2.5 g, 4.8 mmol) was dissolved in 8.0 mL of ethanol and treated with activated charcoal, Darco G-60 (1.25 g). The suspension was stirred at 50° C. for 20 min and then filtered to remove the Darco. To the filtrate was added 10% palladium on activated carbon (250 mg) and the suspension placed on a Parr shaker. The reaction was shaken for 10 h under 30 psi hydrogen gas. The reaction was filtered through celite and concentrated under vacuum to afford compound 1 as a brown gelatinous solid (1.9 g, 4.3 mmol, 91%). $^1$H NMR (300 MHz, DMSO-d$_6$) δ 2.40-2.68 (m, 6H), 2.92-3.18 (m, 2H), 4.35-4.45 (m, 1H), 4.60-4.69 (m, 1H), 5.22-5.30 (m, 1H), 6.82 (s, 1H), 6.85 (s, 1H), 6.68-6.86 (m, 4H), 7.12-7.36 (m, 5H), 7.95 (d, 1H, J=1.4 Hz), 8.19 (s, 1H), 9.49 (br s, 1H). m/z: [M+H$^+$] calcd for $C_{25}H_{29}N_3O_4$ 436.2. found 436.4.

Example 6a

Crystallization of N-{2-[4-((R)-2-hydroxy-2-phenylethylamino)phenyl]ethyl}-(R)-2-hydroxy-2-(3-formamido-4-hydroxyphenyl)ethylamine Dihydrochloride Compound 1 (3.17 g, 7.3 mmol) was dissolved in 111 mL isopropanol in a bath at 50° C. and allowed to cool. The solution was stirred rapidly and 1.0 N HCl was added (24 mL, 24 mmol). The mixture was stirred for 6 h at room temperature. The colorless crystalline product was isolated by filtration and dried under vacuum to afford the dihydrochloride salt of compound 1 (1.71 g, 3.4 mmol, 46%).

Example 6b

Recrystallization of N-{2-[4-((R)-2-hydroxy-2-phenylethylamino)phenyl]ethyl}-(R)-2-hydroxy-2-(3-formamido-4-hydroxyphenyl)ethylamine Dihydrochloride The crystallized dihydrochloride salt of compound 1 from Example 6a (1.5 g, 3.0 mmol) was dissolved in 24 mL of 50% v/v aqueous isopropanol at 50° C. The warm solution was diluted with 48 mL isopropanol and stirred for 2 h. The recrystallized product was isolated by filtration and dried under vacuum to afford 1.0 g of the dihydrochloride salt of compound 1 (2.0 mmol, 66%).

Example 7

Crystallization of N-{2-[4-((R)-2-hydroxy-2-phenylethylamino)phenyl]ethyl}-(R)-2-hydroxy-2-(3-formamido-4-hydroxyphenyl)ethylamine Monohydrochloride In a 500 mL round bottom flask, compound 1 (5.2 g, 11.9 mmol) was dissolved in 187.9 mL isopropyl alcohol with stirring at 40° C. Complete dissolution was achieved within 10 minutes. The flask was then charged with a solution containing 1.0 N HCl (11.3 mL, 11.3 mmol, 0.95 eq.) and H$_2$O (29.6 mL). The solution was stirred and the product crystallized over several hours. After 6 h, the crystals were isolated by filtration and washed with 15 mL ice-cold 15% water in isopropyl alcohol solution followed by 15 mL of isopropyl alcohol. The crystals were dried under house vacuum for 12-16 h to afford the monohydrochloride salt of compound 1 (3.92 g, 8.3 mmol, 70% yield, 98.89% purity by HPLC) as a white crystalline solid. Water content 0.2%, $^1$H NMR (300 MHz, DMSO-d$_6$): δ (ppm) 10.13 (s, 1H), 9.62 (m, 1H), 8.93 (br s, 1H), 8.66 (br s, 1H), 8.27 (d, 1H, J=1.92), 8.13 (d, 1H, J=1.65), 7.21-7.40 (m, 5H), 6.86-6.94 (m, 4H), 6.57 (d, 2H, J=8.52), 6.05 (d, 1H, J=3.57), 5.45-5.55 (m, 2H), 4.80 (m, 1H), 4.70 (m, 1H), 2.70-3.24 (m, 8H). Elemental analysis (wt %) calcd for $C_{25}H_{29}N_3O_4$.HCl: C, 63.62; H, 6.41; N, 8.90; Cl, 7.51. found: C, 63.47; H, 6.54; N, 8.81; Cl, 7.78.

Example 8

Crystallization of N-{2-[4-((R)-2-hydroxy-2-phenylethylamino)phenyl]ethyl}-(R)-2-hydroxy-2-(3-formamido-4-hydroxyphenyl)ethylamine Monohydrochloride In a 200 mL roundbottom flask, compound 1 (200 mg, 0.46 mmol) was dissolved in 40 mL isopropyl alcohol. The solution was stirred and vortexed at room temperature until it became homogeneous. A 7% (w/w) solution of ammonium chloride in water (20 mL, 26 mmol)) was then added dropwise to the stirring solution. The stirring was stopped and the solution was permitted to stand at room temperature for 20 h. White crystals formed. The crystals were collected on a Büchner funnel, washed with 1:1 isopropanol:water (3 mL), and dried for 30 minutes. The crystals were collected to yield the monohydrochloride salt of compound 1 (27 mg, 12% yield).

Example 9

Crystallization of N-{2-[4-((R)-2-hydroxy-2-phenylethylamino)phenyl]ethyl}-(R)-2-hydroxy-2-(3-formamido-4-hydroxyphenyl)ethylamine Monohydrochloride A 250 mL three-necked flask was charged with a hydrochloride salt of compound 1 having 1.52 equivalents of chlorine per mole of compound 1 (6.1 g, 12 mmol) and 1:1 isopropanol:water (98 mL). The mixture was heated to 50-65° C. to dissolve the solid and the solution was stirred at 50-60° C. Isopropanol (98 mL) was slowly added over 30 min at 50-60° C. and the solution was cooled to room temperature over 3 h. Isopropanol (98 mL) was slowly added over 30 min and the solution was stirred at room temperature for 7 h. The crystals were isolated by filtration, washed with isopropanol (30 mL) and dried under vacuum for 16 h to yield the monohydrochloride salt of compound 1 (3.8 g, 8.0 mmol, 67% yield, 99.7% purity by HPLC)

The hydrochloride salt of compound 1 having 1.52 equivalents of chlorine per mole of compound 1 was obtained as follows. Intermediate 6 (3.1 kg), prepared according to the procedures of Examples 1 to 4 was debenzylated according to the process of Example 5, and then crystallized according to the process of Example 6a to afford 2.2 kg of a hydrochloride salt of compound 1. The crystallized product was recrystallized according to the process of Example 6b to afford 1.2 kg of a hydrochloride salt of compound 1 having 1.52 equivalents of chlorine.

Example 10

Crystallization of N-{2-[4-((R)-2-hydroxy-2-phenylethylamino)phenyl]ethyl}-(R)-2-hydroxy-2-(3-formamido-4-hydroxyphenyl)ethylamine Monohydrochloride In a 250 mL flask a hydrochloride salt of compound 1 having 1.52 equivalents of chlorine per mole of compound 1 (5.0 g, 9.8 mmol) was suspended in 1:1 isopropanol:water (79 mL). The slurry was heated in a stepwise fashion, from 50° C. to 70° C. in 5° C. increments, to dissolve the solid. The solution was allowed to cool and isopropanol (80 mL) was added in one portion. Additional isopropanol (80 mL) was added dropwise and crystal formation was observed after about 75 mL was added. The slurry was stirred at room temperature for 16 h. The crystals were isolated by filtration, washed with cold 85% isopropanol/water (10 mL) followed by isopropanol (10 mL) and dried under vacuum to yield the monohydrochloride salt of compound 1.

Example 11

Crystallization of N-{2-[4-((R)-2-hydroxy-2-phenylethylamino)phenyl]ethyl}-(R)-2-hydroxy-2-(3-formamido-4-hydroxyphenyl)ethylamine Monohydrochloride In a scintillation vial, water (10 mL) was added to the dihydrochloride salt of compound 1 (380 mg, 0.75 mmol) to form a slurry which was stirred for 48 h. The pH of the slurry was measured at 1.94. The slurry was vacuum filtered using a Büchner funnel and the filter paper was removed and allowed to air dry for 3 days to yield the monohydrochloride salt of compound 1.

Example 12

Crystallization of N-{2-[4-((R)-2-hydroxy-2-phenylethylamino)phenyl]ethyl}-(R)-2-hydroxy-2-(3-formamido-4-hydroxyphenyl)ethylamine Monohydrochloride In a scintillation vial, water (10 mL) was added to the dihydrochloride salt of compound 1 (402 mg, 0.79 mmol) to form a slurry. The pH was adjusted with 1.0 N NaOH and 1.0 N HCl to 5.09 and the slurry was stirred for 48 h. The pH of the slurry was measured at 5.57. The slurry was vacuum filtered using a Büchner funnel and the filter paper was removed and allowed to air dry for 3 days to yield the monohydrochloride salt of compound 1.

Example 13

Synthesis of crystalline N-{2-[4-((R)-2-hydroxy-2-phenylethylamino)phenyl]ethyl}-(R)-2-hydroxy-2-(3-formamido-4-hydroxyphenyl)ethylamine Monohydrochloride a. Synthesis of 2-Bromo-(R)-1-tert-butyldimethylsiloxy-1-(3-formamido-4-benzyloxyphenyl)ethane A solution of tert-butyldimethylsilyl chloride (40.1 g, 0.26 mol) in dichloromethane (DCM) (37.5 mL) was added to a slurry of imidazole (21.86 g, 0.32 mol) and (R)-2-bromo-1-(3-formamido-4-benzyloxyphenyl)ethanol (74.54 g, 0.21 mol) in DCM (260 mL) over 8 min. The mixture was stirred for 22 h. The reaction was quenched with water (190 mL) and the aqueous layer was extracted with DCM (37.5 mL). The combined DCM layers were distilled at atmospheric pressure to a volume of ca. 110 mL. On cooling, spontaneous crystallisation occurred. Isooctane (750 mL) was added dropwise over 20 min. The slurry was cooled to 0° C. and the solids were collected by filtration then washed with 9:1 v/v isooctane:DCM (3×75 mL) and dried in vacuo to give the title compound as a colorless solid (89.65 g, 90% th). $^1$H NMR in accord with structure (400 MHz, CDCl$_3$) δ (ppm): −0.06 (3H) s; 0.11 (3H) s; *0.12 (3H) s; *0.89 (9H) s; 0.90 (9H) s; *3.38-3.49 (2H) m; 4.78-4.87 (1H) m; *5.09 (2H) s; 5.10 (2H) s; 6.96 (1H) d, J=8.6 Hz; *7.06 (1H) d of d, J=8.3, 2.0 Hz; 7.11 (1H) d of d, J=8.3 Hz, 2.0 Hz; 7.25-7.27 (1H) m; 7.36-7.45 (5H) m; *7.70 (1H) d, J=11.0 Hz; 7.79 (1H) s; 8.38 (1H) d, J=2.0 Hz; 8.42 (1H) d, J=1.5 Hz; *8.76 (1H) d, J=11.8 Hz. * Peaks are due to ca 25M % of the minor rotamer.

b. Synthesis of N-{2-[4-((R)-2-hydroxy-2-phenylethylamino)phenyl]ethyl}-(R)-2-hydroxy-2-(3-formamido-4-benzyloxyphenyl)ethylamine Monohydrochloride 2-[4-((R)-2-Hydroxy-2-phenylethylamino)phenyl]ethylamine (19.8 g, 60 mmol) was dissolved in water (80 mL). Isopropyl acetate (100 mL) was added with stirring. 32% w/v aqueous sodium hydroxide solution (17.2 mL) was added with stirring over 8 min. The organic layer was washed with water (100 mL) then distilled at atmospheric pressure to a volume of ca. 70 mL.

To this solution was added N,N-dimethylacetamide (DMA) (50 mL) followed by 2-bromo-(R)-1-tert-butyldimethylsiloxy-1-(3-formamido-4-benzyloxyphenyl)ethane (20 g, 43 mmol) and potassium carbonate (7.44 g, 54 mmol). The mixture was heated at 90° C. (oil bath temperature) for 17 h then cooled to 50° C. Water (150 mL) was added and the mixture was cooled further to room temperature. 2-Butanone (methylethylketone or MEK) (150 mL) was added and the layers were separated. The organic layer was washed with 17:40:340 v/w/v acetic acid:sodium acetate:water (100 mL) followed by 29% w/v aqueous sodium chloride solution (100 mL). The organic layer was diluted with MEK (50 mL) and then distilled at atmospheric pressure to a volume of ca. 150 mL. More MEK (50 mL) was added followed by a solution of cesium fluoride (8.1 g, 51.6 mmol) in methanol (100 mL). The mixture was heated at 37° C. for 7.5 h then cooled to 30° C. The reaction was quenched with 44% w/v aqueous potassium carbonate solution (100 mL) and water (20 mL) was added. The organic layer was washed with 29% w/v aqueous sodium chloride solution (100 mL) then treated with acetic acid (3.7 mL, 64.6 mmol). The mixture was washed with 29% w/v aqueous sodium chloride solution (100 mL) followed by 6% w/v aqueous sodium chloride solution (3×100 mL).

The solution was diluted with MEK (100 mL) then distilled to a volume of ca. 120 mL. MEK (80 mL) was added and the mixture was seeded. The mixture was distilled again to a volume of ca. 140 mL. More MEK (60 mL) was added and the mixture was cooled to room temperature. The solids were collected by filtration, washed with MEK (3×20 mL) and dried in vacuo to give the title compound as a colorless solid (18.64 g, 77% th). $^1$H NMR in accord of structure (400 MHz, DMSO-$d_6$) δ (ppm): 2.70-2.89 (2H) m; 2.95 (1H) m; 3.01-3.14 (4H) m; 3.14-3.23 (1H) m; 4.71 (1H) m; 4.81 (1H) m; *5.17 (1H) s; 5.23 (1H) s; 5.46 (1H) d, J=4.4 Hz; 5.50 (1H) m; 6.10 (1H) d, J=3.2 Hz; 6.59 (2H) d, J=8.3 Hz; 6.94 (2H) d, J=8.3 Hz; 7.03 (1H) d of d, J=8.6, 2.0 Hz; 7.12 (1H) d, J=8.6 Hz; 7.25 (1H) m; 7.30-7.36 (3H) m; 7.36-7.42 (4H) m; 7.50 (2H) d, J=7.3 Hz; 8.26 (1H) d, J=2.0 Hz; 8.35 (1H) d, J=1.7 Hz; *8.54 (1H) d, J=11.0 Hz; 8.63 (2H) broad res; *9.64 (1H) m; 9.67 (1H) s. * Peaks are due to ca 11.5 M % of the minor rotamer.

Seed crystals were obtained as follows. N-{2-[4-((R)-2-hydroxy-2-phenylethylamino)phenyl]ethyl}-(R)-2-hydroxy-2-(3-formamido-4-benzyloxyphenyl)ethylamine (96.1 mg, 0.18 mmol) was dissolved in 2-propanol (2.2 mL) with warming. A solution of hydrochloric acid in dioxane (4 M, 45 μL, 0.18 mmol) was added. At the end of the addition the majority of material was present as a gum which was stirred at room temperature overnight. The solids were collected by filtration, washed with 2-propanol (3×1 mL) and dried by suction on the filter to give the title compound as a colorless solid (69.5 mg, 69%). $^1$H NMR in accord with structure (400 MHz, DMSO-$d_6$).

c. Crystallization of N-{2-[4-((R)-2-Hydroxy-2-phenylethylamino)phenyl]ethyl}-(R)-2-hydroxy-2-(3-formamido-4-hydroxyphenyl)ethylamine Monohydrochloride A mixture of N-{2-[4-((R)-2-hydroxy-2-phenylethylamino)phenyl]ethyl}-(R)-2-hydroxy-2-(3-formamido-4-benzyloxyphenyl)ethylamine monohydrochloride (40 g) and 5% Pd/C catalyst (Englehard 167, 50% wet with water) (200 mg) in N-methylpyrrolidone (NMP) (120 mL) was stirred under hydrogen at 22±2° C. The mixture was filtered (Whatman GF/F filter) when analysis, by HPLC (detection at 220 nm), of the reaction mixture showed <0.5% (by area) of the starting material. The filter cake was washed with a mixture of NMP and isopropanol (IPA) (1:1) (80 mL).

The combined filtrates were stirred and heated to 69±3° C. Water (10 mL) was added. IPA (100 mL) was added at a rate that maintained the temperature at 69±3° C. Seed crystals (0.8 g) were added. IPA (50 mL) was added over 15 min. The resulting mixture was stirred for about 0.75 h. IPA (250 mL) was then added over about 2.5 h. The resulting slurry was allowed to cool slowly to 20±3° C. and stirred at this temperature for 16 h.

The resulting slurry was cooled to 3±3° C. and stirred at this temperature for 4 h. The slurry was filtered and the collected solid was washed successively with IPA/water (10:1) (80 mL) and IPA (160 mL). The solid was dried under vacuum at ca. 50° C. to give the title compound as a white solid (29.7 g). Yield: 88% th, 74% w/w NMR: δ (ppm): 2.73-2.89 (2H) m; 2.95 (1H) m; 3.01-3.14 (4H) m; 3.15-3.24 (1H) m; 4.72 (1H) m; 4.82 (1H) m; 5.46 (1H) d, J=4.7 Hz; 5.48 (1H) m; 6.03 (1H) d, J=3.4 Hz; 6.59 (2H) d, J=8.6 Hz; 6.89 (1H) d, J=8.1 Hz; 6.91-6.98 (3H) m; *7.01 (1H) d, J=8.6 Hz; *7.14 (1H) s; 7.25 (1H) t, J=7.3 Hz; 7.33 (2H) t, J=7.3, 7.6 Hz; 7.39 (2H) d, J=7.6 Hz; 8.13 (1H) d, J=1.5 Hz; 8.29 (1H) d, J=1.7 Hz; *8.53 (1H) d, J=11.0 Hz; 8.57-9.08 (2H) broad res; *9.36 (1H) d, J=11.0 Hz; 9.60 (1H) s; *9.92 (1H) s; 10.10 (1H) s. * Peaks are due to ca 11 M % of the minor rotamer.

d. Recrystallization of N-{2-[4-((R)-2-Hydroxy-2-phenylethylamino)phenyl]ethyl}-(R)-2-hydroxy-2-(3-formamido-4-hydroxyphenyl)ethylamine Monohydrochloride The title monohydrochloride (5 g) was suspended in aqueous industrial methylated spirit (IMS) (96% ethanol, 4% methanol) (2:1 IMS:water, 72.5 mL) in a 100 mL round bottomed flask. The mixture was warmed to 78° C. to give a clear solution. This was filtered, washed through with aqueous IMS (2:1 IMS:water, 2.5 mL) and the liquor rewarmed to 78° C. to re-dissolve the solid that precipitated during the filtration. The temperature was adjusted to 65° C. and seeded with the title compound (10 mg). The mixture was held at 60-65° C. for 2 h and then cooled to 20-25° C. and stirred at that temperature for 14 h. The suspension was chilled to 0-5° C. and held at that temperature for 3 h. The product was collected via filtration, and washed with aqueous IMS (2:1 IMS:water, 2×7.5 mL) and then IMS (3×7.5 mL) to give the title compound as a white solid, which was dried at 50° C. under vacuum overnight. A DSC trace for this product was obtained with a Perkin Elmer instrument model Pyris 1. Samples were prepared on an aluminum pan, equilibrated at 30° C. and heated at 10° C. per minute to a temperature of 300° C. The instrument was calibrated using indium, tin, and lead standards. The DSC trace shows an absence of discernable endothermic features below about 125° C., with minor endothermic events having onsets at about 133° C., about 151° C., and at about 170° C., and an onset of significant endothermic heat flow at about 229° C.

Example 14

Characterization of N-{2-[4-((R)-2-hydroxy-2-phenylethylamino)phenyl]ethyl}-(R)-2-hydroxy-2-(3-formamido-4-hydroxyphenyl)ethylamine Monohydrochloride The x-ray powder diffraction pattern and differential scanning calorimetry and thermogravimetric traces, both determined at a scan rate of 5° C./min, of the monoHCl salt of compound 1 crystallized from the free base as in Example 7, are shown in FIGS. 1 and 2, respectively.

The characteristic IR peak positions were determined as the average position of the common peaks of samples of the monoHCl salt from Examples 9 and 10: 699±1, 788±1, 810±1, 827±1, 875±1, 970±1, 1026±1, 1056±1, 1080±1, 1101±1, 1213±1, 1296±1, 1374±1, 1441±1, 1546±1, 1596±1, 1660±1, 3371±1, and 3553±1 cm$^{-1}$.

Example 15

Solid State Stability Testing of N-{2-[4-((R)-2-hydroxy-2-phenylethylamino)phenyl]ethyl}-(R)-2-hydroxy-2-(3-formamido-4-hydroxyphenyl)ethylamine Monohydrochloride Samples (250 mg each) of the monoHCl salt of Examples 9 and 10 were stored at 40° C. and 75% relative humidity in open containers and in closed containers. Additional samples (100 mg each) of the monoHCl salt were stored at 50° C. in closed containers. For all storage conditions, after four weeks, there was no observable change in the appearance of the material, analysis by DSC and TGA showed no detectable differences, and analysis by HPLC showed no detectable chemical degradation. Water percentage of the samples stored at 40° C. was less than 0.25% after two and four weeks of storage.

Analytical Methods

X-ray powder diffraction patterns were obtained with a Shimadzu 6000 diffractometer using Cu Kα (40.0 kV, 35.0 mA) radiation. The analysis was performed with the goniometer running in continuous-scan mode of 2°/min with a step size of 0.02° over a range of 4 to 45°. Samples were prepared on glass specimen holders as a thin layer of powdered material. The instruments was calibrated to a silicon metal standard.

The differential scanning calorimetry trace of Example 14, shown in FIG. 2 was obtained with a TA instruments model DSC2010. Samples were placed in sealed aluminum pans for analysis with an empty pan serving as the reference. Samples were equilibrated at 30° C. and heated at 5° C. per minute to a temperature of 300° C. The instrument was calibrated with an indium standard.

Thermogravimetric analysis was conducted using a TA instruments model Q50. Samples were weighed in aluminum pans and heated from 50° C. to 300° C. at a rate of 10° C./min.

The IR spectrum was determined over the wave number (v) range 4000 to 675 $cm^{-1}$ using an Avatar 360 FT-IR spectrometer equipped with a Nicolet omnis sample attenuated total reflection (ATR) sample holder.

$^1$H NMR spectra of Examples 5 and 7 were acquired on a 300 MHz Varian Gemini 2000 spectrometer at ambient temperature. Samples were dissolved in DMSO-d6 and chemical shifts were reported on a TMS scale using residual DMSO protons (2.49 ppm) as reference. $^{13}$C NMR spectra were acquired on JEOL Eclipse$^+$ 400 MHz spectrometer.

HPLC analysis was conducted using a MAC MOD Ace-5, C18, 25 cm×4.6 mm, 5 μm column, equilibrated at 30° C. The mobile phases used were: A: 0.1% TFA in 98:2 water:acetonitrile; and B: 0.1% TFA in 10:90 water:acetonitrile. Detection was by UV absorbance at 244 nm. The initial condition was 6% phase B. A flow rate of 1.0 mL/min and gradients of 6 to 30% B over 25 min, 30% to 60% B in 10 min and 60% to 100% B in 2 min were utilized. The monoHCl salt of compound 1 gave a retention time of 19.1 min.

Mass spectrometric identification was performed by an electrospray ionization method (ESMS) with a Perkin Elmer instrument (PE SCIEX API 150 EX).

Elemental percentages of carbon, hydrogen, and nitrogen are determined by combustion analysis. Percentage of chlorine is determined by potentiometric titration.

Water content was determined by coulometric Karl Fischer titration using a Brinkman Metrohm Karl Fischer Model 831 coulometer.

Chiral purity is determined using a Beckman P/ACE MDQ capillary electrophoresis system. The analysis is performed at pH 2.5 using heptakis-(2,3,-diacetyl-6-sulfato)-β-cyclodextrin (HDAS-β-CD) as the chiral selector and using a 50 μm×31.2 cm fused silica capillary. Detection is by UV absorbance at 200 nm. The four stereoisomers migrate in the following order: SS, RS, SR, RR, where compound 1 is designated as RR.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. Crystalline N-{2-[4-((R)-2-hydroxy-2-phenylethylamino)phenyl]ethyl}-(R)-2-hydroxy-2-(3-formamido-4-hydroxyphenyl)ethylamine monohydrochloride, which is characterized by an x-ray powder diffraction pattern having diffraction peaks at 2θ values of 15.98±0.2, 24.05±0.2, 26.08±0.2, and 28.13±0.2.

2. The compound of claim 1 which is characterized by an x-ray powder diffraction pattern having diffraction peaks at 2θ values of 6.00±0.2, 7.99±0.2, 9.98±0.2, 15.98±0.2, 24.05±0.2, 24.53±0.2, 25.35±0.2, 26.08±0.2, 26.77±0.2, 28.13±0.2, 34.31±0.2, and 38.49±0.2.

3. The compound of claim 1 having an infrared absorption spectrum with significant absorption bands at about 699, 788, 810, 827, 875, 970, 1026, 1056, 1080, 1101, 1213, 1296, 1374, 1441, 1546, 1596, 1660, 3371, and 3553 $cm^{-1}$.

4. The compound of claim 1 which is characterized by a differential scanning calorimetry trace which shows an onset of endothermic heat flow at about 200° C.

5. The compound of claim 1 which is characterized by a differential scanning calorimetry trace which shows an endothermic feature between about 95° C. and 115° C. and an onset of endothermic heat flow at about 200° C.

6. A pharmaceutical composition comprising a therapeutically effective amount of the compound of claim 1 and a pharmaceutically acceptable carrier.

7. The pharmaceutical composition of claim 6, wherein the composition further comprises a therapeutically effective amount of one or more other therapeutic agents.

8. The pharmaceutical composition of claim 6, wherein the composition is formulated for administration by inhalation.

9. A combination comprising the compound of claim 1 and one or more other therapeutic agents.

10. The combination of claim 9 wherein the other therapeutic agent is a corticosteroid, an antichlolinergic agent, or a PDE4 inhibitor.

11. A combination comprising the compound of claim 1 and fluticasone propionate.

12. A combination comprising the compound of claim 1 and 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, or 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

13. A method of treating asthma or chronic obstructive pulmonary disease in a mammal, the method comprising administering to the mammal, a therapeutically effective amount of the compound of claim 1.

14. The method of claim 13 wherein the method further comprises administering a therapeutically effective amount of one or more other therapeutic agents.

15. The method of claim 14 wherein the other therapeutic agent is a corticosteroid, an antichlolinergic agent, or a PDE4 inhibitor.

16. The method of claim 14 wherein the other therapeutic agent is 6α,9α-difluoro-11β-hydroxy-16α-methyl-17α-[(4-methyl-1,3-thiazole-5-carbonyl)oxy]-3-oxo-androsta-1,4-diene-17β-carbothioic acid S-fluoromethyl ester, or 6α,9α-difluoro-17α-[(2-furanylcarbonyl)oxy]-11β-hydroxy-16α-methyl-3-oxo-androsta-1,4-diene-17β-carbothioic acid S-fluoromethyl ester.

* * * * *